(12) United States Patent
Nagarkar et al.

(10) Patent No.: US 8,618,795 B1
(45) Date of Patent: Dec. 31, 2013

(54) SENSOR ASSEMBLY FOR USE IN MEDICAL POSITION AND ORIENTATION TRACKING

(75) Inventors: Kaustubh Ravindra Nagarkar, Clifton Park, NY (US); William Hullinger Huber, Niskayuna, NY (US); Daniel Eduardo Groszmann, Belmont, MA (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 13/538,573

(22) Filed: Jun. 29, 2012

(51) Int. Cl.
*G01R 33/02* (2006.01)
*G01B 7/14* (2006.01)
*G01R 33/12* (2006.01)
*H01L 29/12* (2006.01)

(52) U.S. Cl.
USPC ...... 324/252; 324/207.21; 324/228; 428/620; 252/62.3 C

(58) Field of Classification Search
USPC .......................................................... 324/252
See application file for complete search history.

(56) References Cited

U.S. PATENT DOCUMENTS

| | | | |
|---|---|---|---|
| 6,090,498 A * | 7/2000 | Omata et al. | 428/811.2 |
| 6,268,662 B1 | 7/2001 | Test et al. | |
| 6,891,367 B2 * | 5/2005 | Shinmura et al. | 324/252 |
| 7,115,446 B2 * | 10/2006 | Koo et al. | 438/125 |
| 7,273,803 B2 * | 9/2007 | Cheng et al. | 438/612 |
| 7,451,651 B2 | 11/2008 | Woychik et al. | |
| 2004/0184196 A1 * | 9/2004 | Jayasekara | 360/319 |
| 2005/0122101 A1 * | 6/2005 | Bohlinger et al. | 324/252 |
| 2006/0145715 A1 * | 7/2006 | Salmon | 324/754 |
| 2008/0008900 A1 * | 1/2008 | Cheng et al. | 428/620 |
| 2010/0053423 A1 | 3/2010 | Singh | |
| 2010/0127696 A1 | 5/2010 | Huber et al. | |
| 2010/0249571 A1 | 9/2010 | Jensen et al. | |
| 2011/0151587 A1 | 6/2011 | Huber | |

FOREIGN PATENT DOCUMENTS

WO 2010117383 A1 10/2010
WO 2011097422 A1 8/2011

OTHER PUBLICATIONS

J.R. Davis, ASM Specialty Handbook, Nickel, cobalt and their Alloys, Copyright 2000 by ASM International, p. 9 listed as uses of Nickel.*
STIC Search Report.*
McTaggart, V., et al., Stud Bumping and Die Attach for Expanded Flip Chip Applications, Advanced Packaging, pp. 1-3, Sep. 2004.

* cited by examiner

*Primary Examiner* — Jermele M Hollington
*Assistant Examiner* — Christopher McAndrew
(74) *Attorney, Agent, or Firm* — Fletcher Yoder, P.C.

(57) ABSTRACT

A sensor assembly is provided for use in tracking a medical device. The sensor assembly comprises a magnetoresistance sensor capable of providing position and orientation information. In certain implementations, the magnetoresistance position and orientation sensor is originally configured for connection to a substrate using one type of interconnect approach but is modified to be connected using a different interconnect approach.

19 Claims, 8 Drawing Sheets

SENSOR ASSEMBLY FOR USE IN MEDICAL POSITION AND ORIENTATION TRACKING

BACKGROUND

The subject matter disclosed herein relates generally to sensors that may be used to provide position and orientation information for an instrument, implant or device used in a medical context, such as in a surgical or interventional context. In particular, the subject matter relates to a sensor assembly sized to fit within a medical instrument, implant or device.

In various medical contexts it may be desirable to acquire position and/or orientation information for a medical instrument, implant or device that is navigated or positioned (externally or internally) relative to a patient. For example, in surgical and/or interventional contexts, it may be useful to acquire position and/or orientation information for a medical device, or portion of a medical device, even when the device or relevant portion is otherwise out of view, such as within a patient's body. Likewise, in certain procedures where an imaging technique is used to observe all or part of the position and orientation information, it may be useful to have position and orientation information derived from the tracked device itself that can be related to the image data also being acquired.

One issue that can arise with respect to navigation sensors suitable for acquiring position and orientation information in this manner is the size of the position and orientation sensor relative to the device that is to be tracked. In particular, in surgical and interventional contexts, it may be desired to use an instrument, implant or device that is as small as possible, either due to the size and/or fragility of the anatomy undergoing the procedure or to otherwise minimize the trauma associated with the procedure. Therefore, it may also be desirable to use a navigation sensor that is suitably sized for the instruments, implants or devices being employed. However, it may be difficult to construct a suitable position and orientation sensor assembly that provides the desired position and orientation information with the desired precision and accuracy and which is of a suitable size for use with or within the instruments, implants or devices in question.

BRIEF DESCRIPTION

In accordance with one embodiment, a position and orientation sensor assembly is provided. The sensor assembly includes a magnetoresistance sensor array comprising a plurality of contact pads. The plurality of contact pads are not configured to be connected by a solder connection. The position and orientation sensor assembly also includes a plurality of metallization layers deposited on each of the plurality of contact pads. Each metallization layer comprises at least one solderable layer. The position and orientation sensor assembly also includes a printed circuit substrate comprising a plurality of contacts corresponding to the plurality of contact pads and a solder material connection formed between each respective solderable layer on the position and orientation sensor and a corresponding contact of the plurality of contacts.

In accordance with an additional embodiment, a method is provided for fabricating a position and orientation sensor assembly. The method includes the act of applying a solderable layer over a contact pad of a die. The contact pad is not suitable for receiving a soldered connection. Solder material is disposed over each solderable layer. The solder material is reflowed to electronically connect the contact pad of the die with a corresponding contact of a printed circuit substrate.

In accordance with a further embodiment, a medical instrument is provided. The medical instrument comprises an insertion portion configured to be inserted into a patient and a body portion in communication with the insertion portion. The body portion is configured to allow an operator to manipulate or operate the insertion portion with respect to the patient. The medical instrument also comprises a position and orientation sensor assembly positioned within the insertion portion. The position and orientation sensor assembly comprises at least one one-axis or two-axis magnetoresistance sensor configured to generate position and orientation information in the presence of an externally applied magnetic field and a printed circuit substrate connected to the two-axis magnetoresistance sensor by a flip chip interconnection.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

As discussed herein, a position and orientation sensor assembly is discussed that is suitable for use in a medical device, implant or instrument. In certain embodiments, the sensor assembly may include a magnetoresistance sensor, such as a two-axis electromagnetic sensor, providing six-degrees of freedom. In implementations where the position and orientation sensor is originally configured for wire bonding to an interposer that is subsequently soldered to a printed circuit board, contact pads on the sensor may be unsuitable for a soldered connection. The position and orientation sensor may, therefore, be modified by the application of various additional metallization layers so that the sensor may be interconnected directly to a substrate using an approach better suited for achieving a small form factor for the finished sensor assembly, such as a flip chip approach. For example, in implementations where the original position and orientation sensor has interconnect pads that are aluminum or of some other composition suitable for wire bonding, various metallization layers may be added so that the sensor may be connected to a substrate using a different interconnect approach, such as a flip chip approach.

Figure 1:
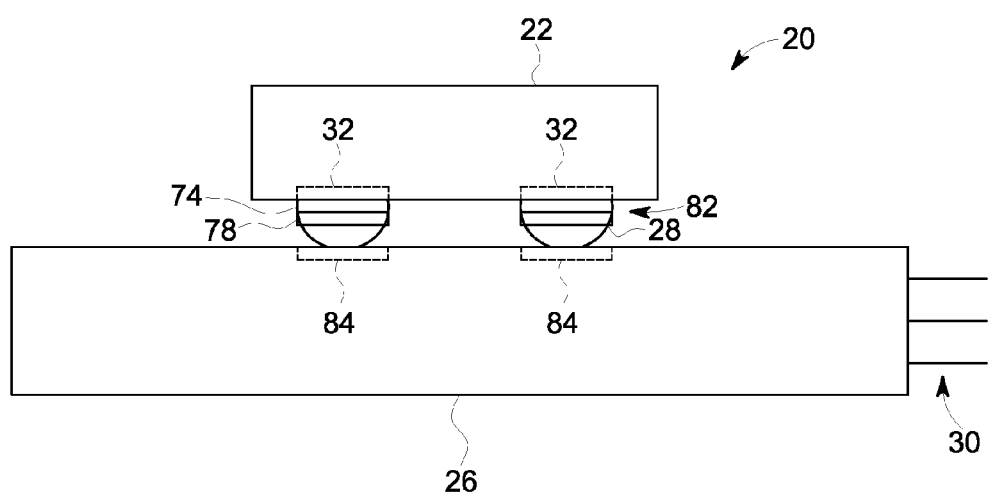
FIG. 1 depicts a position and orientation sensor assembly, in accordance with aspects of the present disclosure.

With the foregoing in mind, and turning to FIG. 1, an example of a position and orientation sensor assembly 20 is depicted in accordance with aspects of the present approach. In one embodiment, the sensor assembly includes a magnetometer or magentoresistive sensor arrangement, such as an integrated two-axis sensor array 22 suitable for providing position and/or orientation information in the presence of an external magnetic field. Such a magnetoresistance sensor can be available in the form of a wafer on which many such sensors are formed and which may be commercially available. In one implementation, the position and orientation sensor array 22 is a solid-state (i.e., silicon based) device having a respective magnetic sensor for each of two perpendicular axes (i.e., two perpendicular magnetic sensors). In combination, the two magnetic sensors of the sensor array 22 are sufficiently sensitive to generate position (i.e., x, y, and z position data) and orientation data (i.e., roll, pitch, and yaw orientation data) in the presence of a magnetic field. In certain implementations, the position and orientation sensor array 22 is provided and processed as a die of a wafer, as discussed below, and operates at a low voltage (e.g., 2.0 V or less) and over a wide magnetic field range (e.g., ±10 Oe). Further, in certain implementations the position and orientation sensor array 22 has a very low noise floor at metal tolerant frequencies (e.g., 10-1000 times lower than microcoils) and has a compact form factor (e.g., as small as about 0.4 mm in width).

In practice, the position and orientation sensor array 22 may be a multi-layer design, such as having layers corresponding to an offset strap used to calibrate the sensor array 22, a resistor bridge, and a set-reset strap allowing the respective magnetic sensors of the array 22 to be reset, if needed. Therefore, the sensor array 22 may include pads 32 (see FIGS. 2A-2D and FIG. 3) or contacts corresponding to sensor inputs and outputs for the respective perpendicular magnetic sensors, set-reset operations for the respective perpendicular magnetic sensors, offset or calibration operations, for the respective perpendicular magnetic sensors, power, ground and so forth.

In one implementation, the respective pads or contacts of the position and orientation sensor array 22 are configured or designed to be wire bonded to an interposer or circuit. The interposer is typically of a larger footprint than the sensor to accommodate the wire bonds. The sensor is encapsulated on the interposer to form an electronic package. The electronic package is then typically picked and placed and soldered to the printed circuit board as a lead frame package or a Ball Grid Array (BGA) interconnect package. However, to obtain a useful form factor for use with or within an interventional or therapy or diagnostic device, implant or instrument, it may instead be desired to use a different interconnect approach, such as a flip chip or direct chip attachment approach, to more compactly connect the sensor array 22 to a flexible or rigid printed circuit substrate 26 capable of being affixed to or within the device, implant or instrument in question. In such a flip chip approach, reflowable bumps or solder balls 28 may be provided on or in communication with pads 32 of the sensor array 22 and corresponding pads or contacts on the substrate 26. The sensor is directly connected to the printed circuit substrate without any pre-packaging with an interposer.

The substrate 26 may, in turn include or be connected to one or more wires, traces, flex-circuits, connectors, or other conductive structures 30 that allow data to be read out from the electrically connected sensor array 22. Likewise, the conductive structures 30 may allow the sensor array 22 to be powered, as needed, by an external power source or battery. One example of a substrate 26 is a printed circuit board (PCB) having provided contacts corresponding to those of the sensor array 22.

Turning to FIGS. 2A-2F, a process flow diagram is provided describing one implementation in which a position and orientation sensor array 22 that is originally configured to be electrically connected by one interconnect arrangement (e.g., wire bonding) is processed and connected using a different interconnect arrangement (e.g., flip chip). By way of example, the pads 32 of the sensor array 22 may initially be finished using aluminum or a primarily aluminum composition (e.g., 98% aluminum, 2% copper) that is suitable for a wire bond approach but not suitable for a flip chip approach. Thus, in such an implementation, the pads 32 may undergo a metallization process, as discussed below, to create a metal stack over each pad 32 that is more suitable for the desired interconnect approach.

Figure 2A:
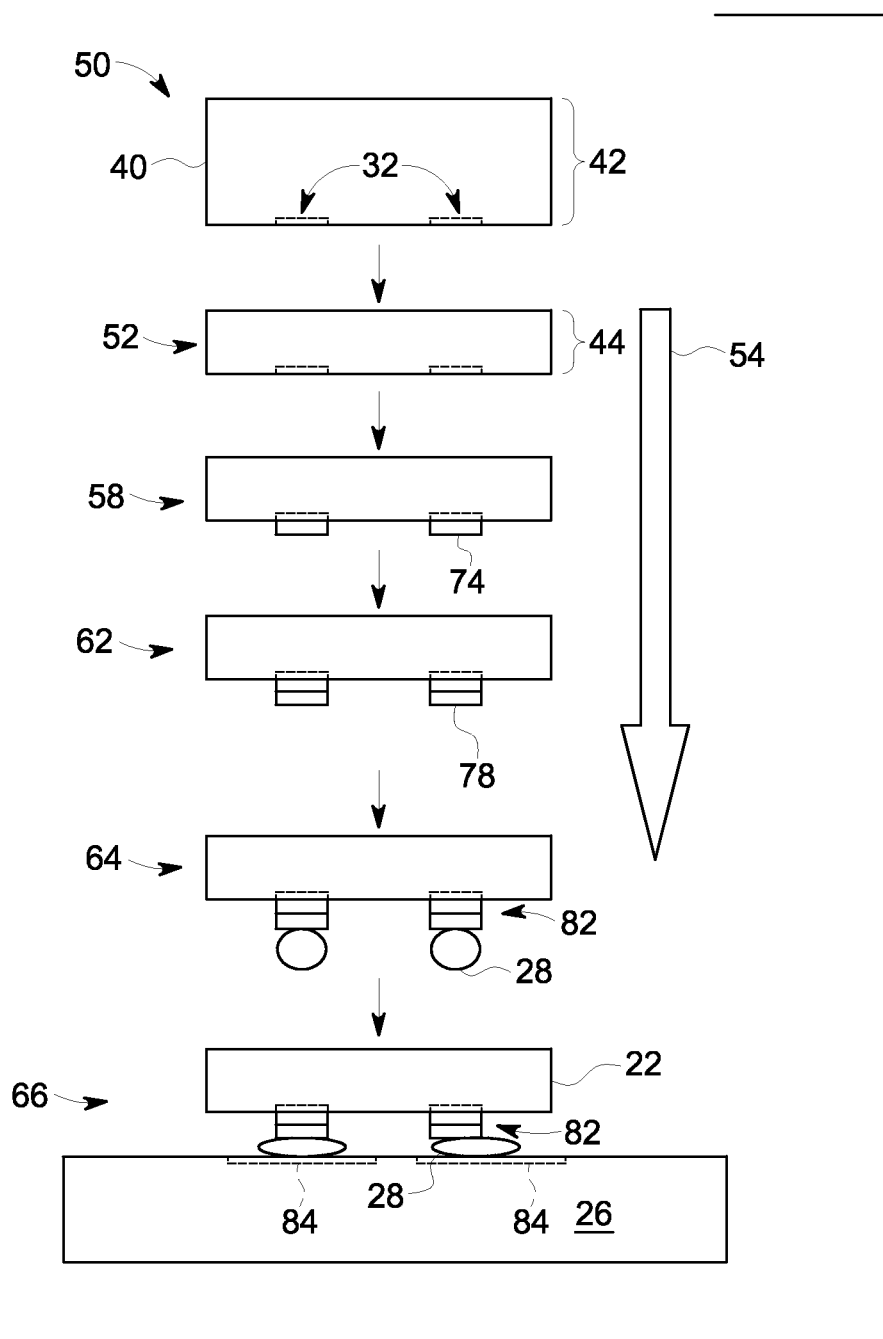
FIG. 2A is a process flow diagram depicting steps in forming a position and orientation sensor assembly, in accordance with aspects of the present disclosure.

The depicted process 50 of FIG. 2A begins with a bare die 40 (FIGS. 2A and 2B) that may correspond to a stock or general version of the sensor array 22. In practice, the bare die may actually be provided as part of a wafer that includes tens, hundreds, or thousands of such dies 40. Thus, operations discussed herein as being performed on a die may actually be performed at the wafer level, prior to cutting the individual dies, so as to increase the efficiency of the process. For example, the processes discussed herein may be performed at the wafer level using lithographic masking, metallization, and etching techniques.

Figure 2B:
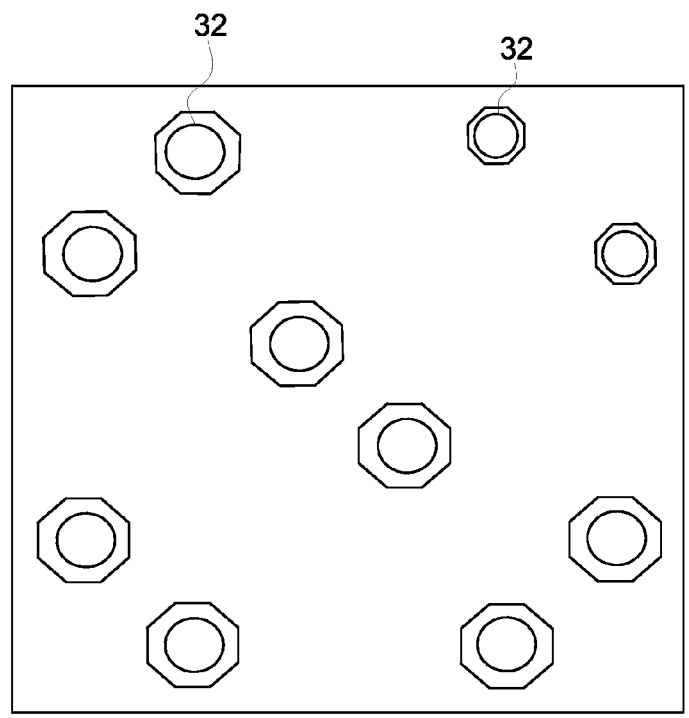
FIG. 2B depicts a plan view of a bare die, as described in FIG. 2A.
Figure 2C:
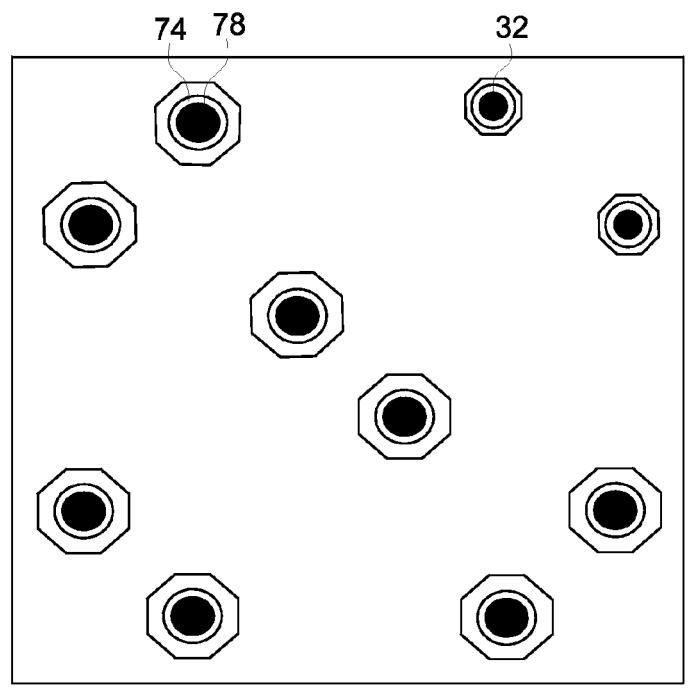
FIG. 2C depicts a plan view of a metalized die, as described in FIG. 2A.

As depicted in FIGS. 2A and 2B, the bare die 40 includes conductive pads 32 that are generally flush with a surface of the die 40. In other implementations, the pads 32 may not be flush with the surface of the dies and may have some elevation with respect to the surface of the die. In one implementation, the pads 32 are approximately between 30µ to 40µ in radius and have a pitch (i.e., inter-pad spacing) between about 100µ to about 200µ.

Further, in the depicted embodiment, the bare die 40 has an associated thickness 42 that is greater than the thickness desired for the final configuration of the sensor array 22. Thus, in such an implementation, a portion of the bare die 40 may be removed or thinned (step 52) from a surface opposite the surface with the pads 32 to achieve a desired thickness 44 for the die and, thereby for the sensor array 22 being produced. By way of example, the portion of the die may be removed by chemical means (e.g., etching) or mechanical means (e.g., planarization). In one implementation, the bare die 40 is initially about 750µ thick and is thinned down to about 200µ or less (e.g., 50µ).

To facilitate a flip chip interconnection, the pads 32 that are intended for wire bond connection are modified via a series of underbump metallization steps (steps 54) to form respective metal stacks on each pad 32 that can be connected to the substrate 26 by a respective solder ball or solder bump. In the depicted example, a solderable layer 74 is deposited (step 58). The solderable layer 74 promotes soldering of the solder bumps to the sensor pads. In one embodiment, the solderable layer 74 is or includes electroless nickel. In certain implementations the solderable layer 74 is about 3 micron to 5 micron in thickness. The addition of the electroless nickel solderable layer may be performed without a lithography mask in at least one embodiment.

The next metallization layer added to the metal stack 82 being formed (step 62) in the depicted example is a corrosion resistance layer 78. In one embodiment, the corrosion resistance layer 78 is or includes gold. In certain implementations the corrosion resistance layer 78 is about 500 Å to about 1000 Å in thickness. As will be appreciated, in certain embodiments where different under bump metallization techniques are employed, a mask may present during all or part of the metallization process 54.

Figure 2D:
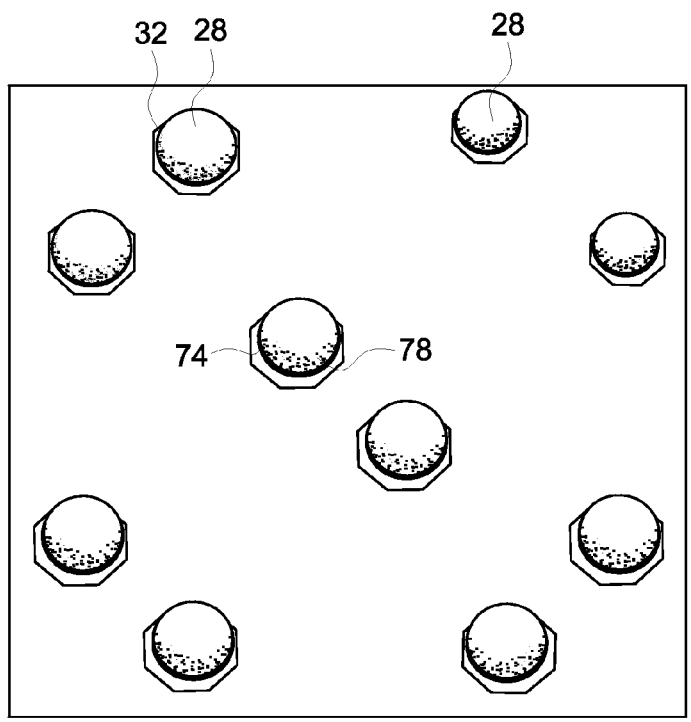
FIG. 2D depicts a plan view of a metalized die with solders balls deposited on the respective pads, as described in FIG. 2A.
Figure 2E:
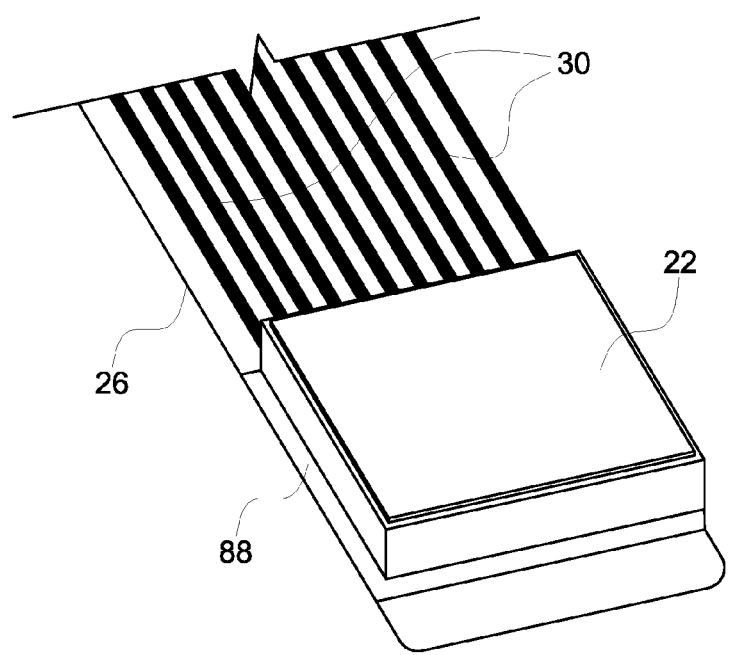
FIG. 2E depicts a position and orientation sensor array placed on a substrate, as described in FIG. 2A.

In one implementation, solder balls 28 are positioned or formed (step 64) on the metal stack 82 (FIGS. 2A and 2D). In other implementations, solder bumps may be formed on the metal stack 82. Various processes may be employed to form the solder balls on the metal stack 82. For example, the solder balls 28 may be mechanically dropped or placed on the stack 82, may be applied by a jetting process, and/or may be screen printed onto the respective stacks 82. If needed, after application of the solder material, the applied material may be formed into balls 28 by a reflow process, i.e., application of sufficient heat so as to cause softening and flowing of the solder material into a solder ball. In one implementation a solder ball has a diameter of about 5μ when formed.

In certain implementations, the above processes may be performed on a wafer containing multiple dies so as to allow efficient production and processing of multiple dies at one time. Prior to performing a flip chip assembly process, the respective dies are cut from the wafer material such that each die is a separate and discrete unit, i.e., a sensor array 22. A quality control check of each die may be performed prior to the cutting operation.

Figure 2F:
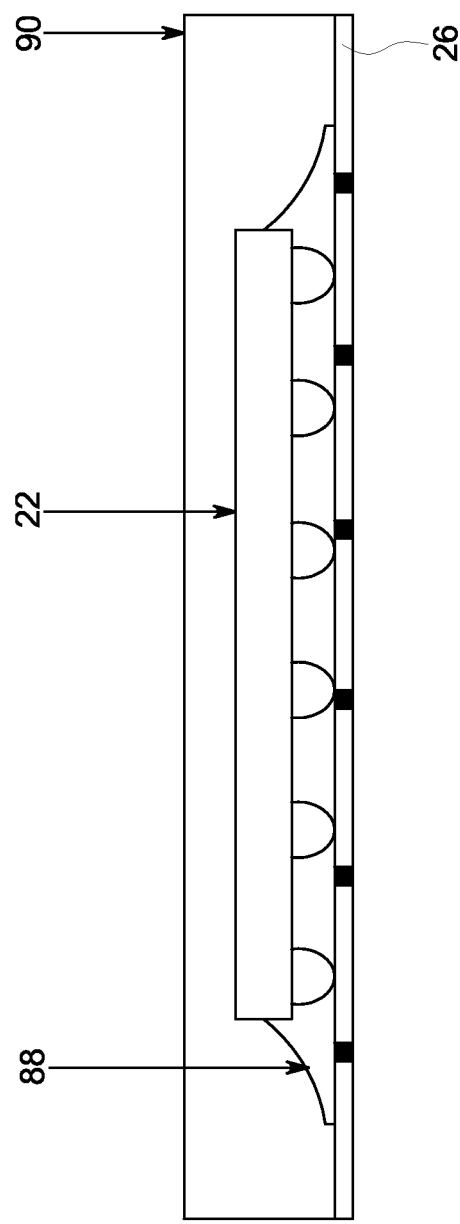
FIG. 2F depicts a cross-sectional view of the position and orientation sensor array and substrate of FIG. 2E.

Once cut, the sensor array 22 may be flipped or inverted and assembled (step 66) directly to a printed circuit board, i.e., substrate 26 (FIGS. 2E and 2F), to form a position and orientation sensor assembly 20. In particular, connection between a sensor array 22 and substrate 26 may be established by reflowing the solder balls 26 positioned over the pads 32 to establish contact with corresponding contacts 84 on the substrate 26. One advantage provided by using a flip chip interconnect approach (as opposed to other approaches, such as wire bond) is that the flip chip approach provides some degree of self-alignment of the sensor array 22 with respect to the substrate 26. This results in a precise, repeatable alignment of the sensor array 22 on the substrate 26. In particular, as the solder melts, small misalignments between the sensor array 22 and substrate 26 can be mitigated due to the wettability of the solder on the respective solderable surfaces. That is, the solder, when undergoing reflow, flows to the appropriate contact spots so as to establish a useful connection. This self-alignment aspect of a flip chip assembly approach provides greater tolerance with respect to the initial mechanical alignment of the sensor array 22 and substrate 26 being connected as well as the final alignment within the medical instrument, implant or device. After assembly of the sensor assembly 20, an underfill material 88 (e.g., an epoxy) may be applied to the sensor assembly 20 to fill some or all of the open space between the sensor array 22 and the substrate 26, thereby providing additional thermomechanical stability. As depicted in FIG. 2F, which depicts a cross-section of a finished sensor assembly, a mold cap 90 or other covering or protective layer may be deposited or coated on the sensor array 22 and substrate 26 so as to provided additional protection and/or stability to the finished assembly.

While the preceding discussion describes the use of reflow capable solder as the attachment or connection medium, in other implementations, other mechanisms may be employed to attach the position and orientation sensor array 22 to the substrate 26. By way of example, in other embodiments a flip chip interconnection may be made to the printed circuit board using other approaches. For example, a gold stud bump method may be employed to form the interconnections described herein. In one such implementation, a gold stud bump is applied directly to the non-solderable pads 32 (e.g., pads configured for wire bonding) on the position and orientation sensor 22. Application of the gold stud bump may be accomplished by various approaches. For example, in a first approach the stud bumped position and orientation sensor may be connected to the printed circuit board using thermocompression or thermosonic bonding. In this approach, the printed circuit board has a gold plated layer than enables the formation of the bond. In a second approach, the stud bump position and orientation sensor is connected to the printed circuit board using an Anisotropic Conductive Paste or Film (ACP or ACF) or an Electrically Conductive Adhesive (ECA). In such approaches, the ACF, ACP, or ECA provide mechanical as well as electrical interconnection between the position and orientation sensor and the printed circuit board. In a further approach, the stud bump sensor is connected to the printed circuit board using a non-conducting epoxy adhesive (NCA). In this approach, the NCA establishes a firm mechanical contact between the gold stud bump and the metal pad on the printed circuit board thereby enabling an electrical contact. The cured NCA provides mechanical integrity to the assembly. Alternatively, a gold plated pad method may be employed to form the interconnects discussed herein. For example, in one such implementation gold-plated raised features are applied to the non-solderable pads on the sensor. The plated sensor is connected to the printed circuit board using ACP, ACF, ECA, or NCA approaches as described above. The preceding discussion merely describes one example of suitable steps that may be performed in modifying a position & orientation sensor array die that is originally intended for use with one interconnection approach (e.g., wire bond) so that the position and orientation sensor array die can be directly connected to a rigid or flexible printed circuit board using a different interconnection approach (e.g., flip chip). As will be appreciated, in practice certain of these steps may be omitted, additional steps may be performed, and/or the order of the discussed steps may be altered. Indeed, the described steps are provided merely to facilitate explanation and to describe one suitable, non-limiting example of an approach for fabricating a position and orientation sensor assembly.

Figure 3:
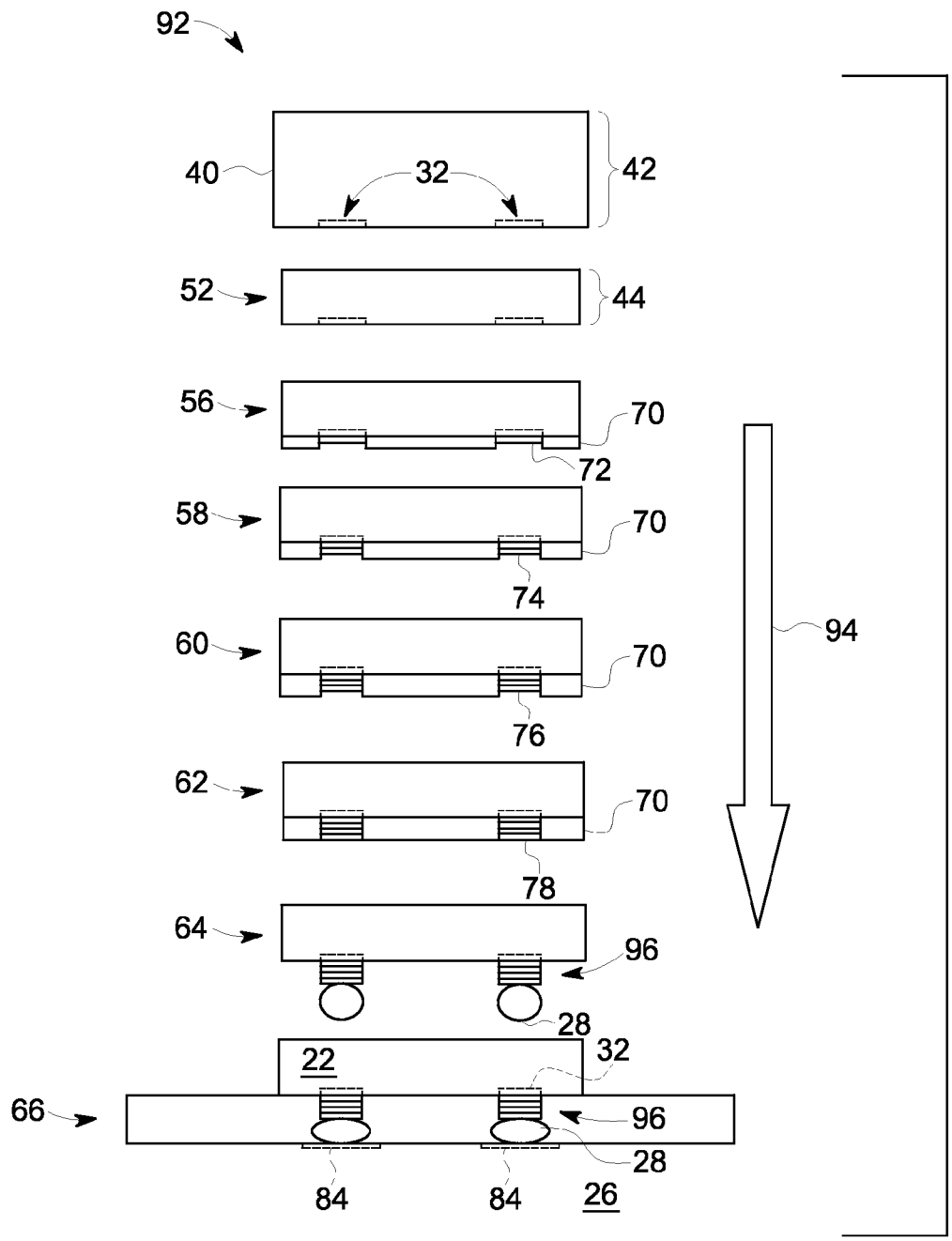
FIG. 3 is a process flow diagram depicting an alternative implementation for forming a position and orientation sensor assembly, in accordance with aspects of the present disclosure.

Turning to FIG. 3, a further embodiment 92 is depicted in which one or more additional metallization layers are added in an alternative underbump metallization process 94. For example, in certain implementations an adhesion promoter layer 72 is deposited (step 56) on the pads 32 prior to deposition of the solderable layer 74. In such an implementation, the adhesion promoter layer 72 may facilitate adhesion of the subsequent metallization layers, such as solderable layer 74, to the base pad material. In one embodiment, the adhesion promoter layer 72 is or includes titanium or titanium oxide and is about 10 nm to about 100 nm in thickness.

In addition, in the depicted example a diffusion barrier 76 is also deposited (step 60), such as between solderable layer 74 and corrosion resistance layer 78. In such an implementation, the diffusion barrier layer 76 helps to prevent diffusion between separated layers. In one embodiment, the diffusion barrier layer 76 is or includes electroless nickel. In certain implementations the diffusion barrier layer 76 is about 500 Å to about 1000 Å in thickness. In the depicted example, a metallization stack 96 comprising layers such as an adhesion promoter layer 72, solderable layer 74, diffusion barrier layer 76, and/or corrosion resistance layer 78 is formed by the underbump metallization process 94. Contact may be formed between the metallization stack 96 and contact 84 of the substrate 26 as discussed above, such as via solder bumps or balls 28.

In a different embodiment, the pads 32 on the die may be re-configured using redistribution layers prior to adding the solderable layer 74 and the corrosion resistance layer 78. A dielectric layer is added on the surface comprising the non-solderable pads. The dielectric layer is removed in the areas where the pads are located to expose the pads 32. A metallization layer is added on the surface of the dielectric layer. The metallization layer is etched to create routings that re-position the location of the pads. Another dielectric layer is added on top of the metallization layer. The dielectric layer is then removed to expose the metallization at the locations where the new pads are desired. A solderable layer 74 is deposited on top of the exposed metallization. A corrosion resistance layer 78 is deposited on the solderable layer 74.

Figure 4:
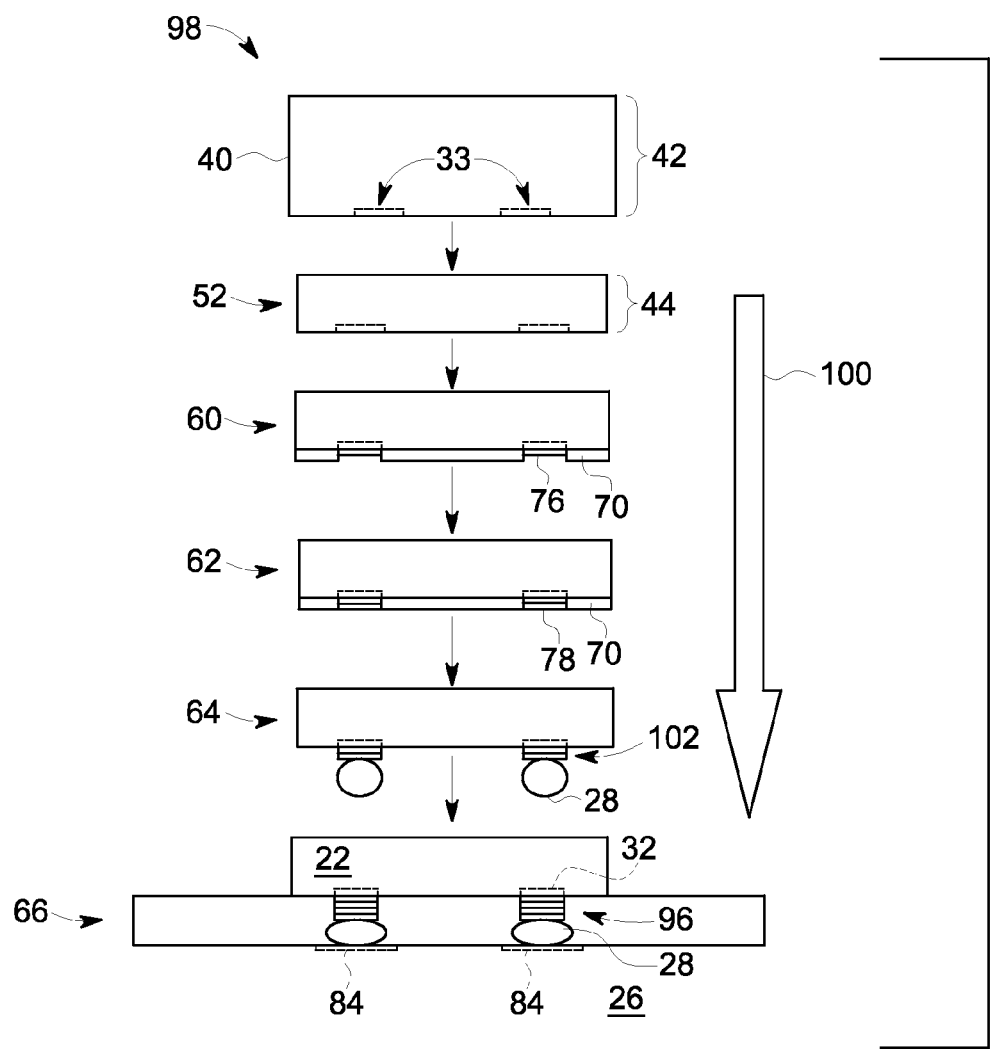
FIG. 4 is a process flow diagram depicting a further implementation for forming a position and orientation sensor assembly, in accordance with aspects of the present disclosure.

Turning to FIG. 4, a process flow diagram is provided demonstrating a further approach 98 by which a position and orientation sensor assembly may be formed. In this example, the bare die 40 is formed with contact pads 33 that are suitable for a solder based connection, (e.g., copper contact pads). In this example, certain of the steps discussed with respect to FIG. 2A may be altered to allow for the suitability of contact pads 33 for forming a solder-based connection. Further, to illustrate a mask-based deposition approach, one or more masks 70 are depicted that limit or guide the deposition of a layer of material to the pads 33. To simplify explanation, a single masking process is described. However, as will be appreciated, any lithographically suitable approach to limiting deposition of a metal layer to particular locations or of removing unwanted deposited material from unwanted locations may be employed, as may any number of distinct masking operations.

In the depicted example, a metallization process 100 is performed on the pads 33. In the depicted metallization process 100 a barrier layer deposition step 60 is performed to deposit a diffusion barrier layer 76. In the depicted example, a subsequent corrosion resistance deposition step 62 is performed to apply a corrosion resistance layer 78. However, in other embodiments, the diffusion barrier layer 76 may also be omitted. Further, in yet other embodiments, no metallization may be performed and the solder balls 28 may be formed or deposited directly on the contact pads 33. As a result of the depicted metallization processes, a metallization stack 102 is formed by the metallization process 100. Contact may be formed between the metallization stack 102 and contact 84 of the substrate 26 as discussed above, such as via solder bumps or balls 28.

Figure 5:
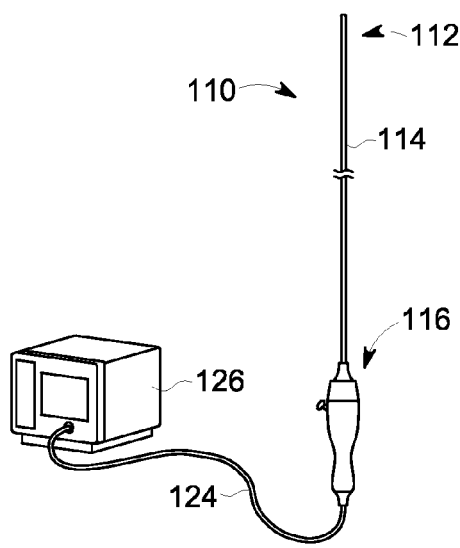
FIG. 5 depicts an example of an interventional device suitable for use with one or more of the position and orientation sensor assembly of FIG. 1, in accordance with aspects of the present disclosure.

Turning to FIG. 5, an example of a medical device is depicted that is suitable for use with a position and orientation sensor assembly 20 as discussed herein. In this example, the medical device is a catheter 110 suitable for insertion into and navigation through the vasculature of a patient. As will be appreciated, though a catheter is provided by way of example, the position and orientation sensor assembly 20 discussed herein may be provided on or in various other types of surgical or interventional instruments, implants or devices. Examples of such instruments, implants or devices include, but are not limited to: implant, probe, awl, drill, aspirator, forceps, blade, screw, nail, pin, k-wire, needle, cannula, introducer, catheter, guidewire, stent, heart valve, filter, endoscope, laparoscope, or electrode, endoscopes or other intrabody camera devices, or any other suitable device for which position and orientation information may be desired during surgical or interventional use.

Turning back to FIG. 5, the depicted catheter includes a distal end or tip 112 in which the position and orientation sensor assembly 20 may be positioned as well as a shaft 114 in communication with the tip 112 and which connects the tip 112 with a handle assembly 116 that may be used to manipulate and operate the catheter 110. In certain instances, the handle may communicate, such as via cable 124, with an operator console 126 that allows a user to control certain aspects of the catheter function and operation.

Figure 6:
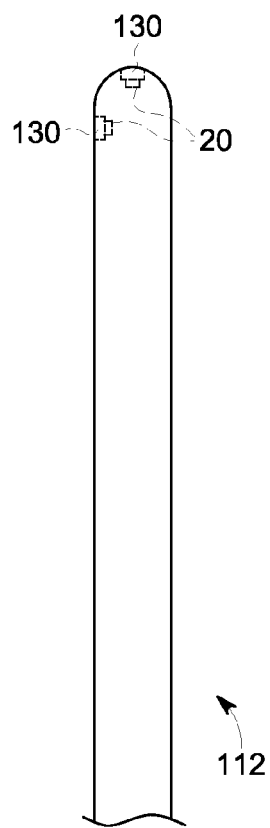
FIG. 6 depicts a distal end or tip of the interventional device of FIG. 4, in accordance with aspects of the present disclosure.

Turning to FIG. 6, a close-up view of the tip 112 of catheter 110 is provided. In this depiction, two position and orientation sensor assemblies 20 are depicted as being positioned within the tip 112. For example, the sensor assemblies may be potted or otherwise affixed (such as by epoxy or potting material 130) into the desired position within the catheter tip 112. While two position and orientation sensor assemblies 20 are shown by way of example, in other embodiments a single sensor assembly 20 may be provided while, in yet other implementations three, four, or more sensor assemblies 20 may be provided in the medical device. Further, to achieve the desired placement and orientation of a sensor assembly 20 in the device (e.g., tip 112), one or both of the sensor assembly 20 and the portion of the device where the sensor assembly 20 is to be placed may be keyed to allow placement on the position and orientation sensor assembly 20 in suitable locations and/or orientations.

In certain implementations, the position and orientation sensor array 22 may be commercially available and relatively inexpensive. As a result, devices or instruments in which the sensor assemblies 20 are installed may be made to be used only once and then disposed of. That is, the cost of the position and orientation sensor assembly 20 is low enough that the position and orientation sensor assembly 20 and devices in which it is installed may be made to be disposable without the cost being prohibitive.

Technical effects of the disclosed embodiments include forming a small form factor position and orientation sensor assembly 20. In one implementation, the position and orientation sensor assembly 20 includes a two-axis magnetoresistance sensor array 22 originally configured for wire bond attachment to a substrate or an interposer that forms an electronic package, where the position and orientation sensor array 22 is modified so as to allow flip chip or direct chip attachment to the substrate 26. Further technical effects include the manufacture of surgical and/or interventional medical instruments, implants or devices incorporating at least one magnetoresistance sensor capable of providing 3 degrees of position information and 3 degrees of orientation information. A further technical effect is the manufacture of single-use or otherwise disposable surgical and/or interventional medical instruments, implants or devices incorporating at least one magnetoresistance sensor.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A position and orientation sensor assembly, comprising:
a magnetoresistance sensor array comprising a plurality of contact pads, wherein the plurality of contact pads are not configured to be connected by a solder connection;
a plurality of metallization layers deposited on each of the plurality of contact pads, wherein each plurality of metallization layers comprises at least one solderable layer and an adhesion promoter layer disposed between the at least one solderable layer and a respective contact pad, and wherein the adhesion promoter layer comprises titanium or titanium oxide, and wherein each of the plurality of metallization layers comprises a corrosion resistance layer, wherein the corrosion resistance layer is or includes gold, and a diffusion barrier layer disposed between the at least one solderable layer and the corrosion resistance layer, and wherein the solderable layer is disposed between the adhesion promoter layer and the diffusion barrier layer;
a printed circuit substrate comprising a plurality of contacts corresponding to the plurality of contact pads; and
a solder material connection formed between each respective solderable layer and a corresponding contact of the plurality of contacts.

2. The position and orientation sensor assembly of claim 1, wherein the magnetoresistance sensor comprises a two-axis sensor array configured to generate position and orientation information in the presence of a magnetic field.

3. The position and orientation sensor assembly of claim 1, wherein the plurality of contact pads of the magnetoresistance sensor array are configured to be connected via wire bonding.

4. The position and orientation sensor assembly of claim 1, wherein the solder material connections self-align with the respective contacts of the plurality of contacts.

5. The position and orientation sensor assembly of claim 1, comprising an underfill material disposed at least in part between the magnetoresistance sensor array and the printed circuit substrate.

6. A method of fabricating a magnetoresistance sensor assembly, comprising:
applying an adhesion promoter layer over a contact pad of a magnetoresistance sensor die, wherein the contact pad is not suitable for receiving a soldered connection;
applying a solderable layer over the adhesion promoter layer, wherein the adhesion promoter layer comprises titanium or titanium oxide;
applying a diffusion barrier layer over the solderable layer;
applying a corrosion resistance layer, wherein the corrosion resistance layer is or includes gold, over the diffusion barrier layer,
disposing solder material over the diffusion barrier layer; and
reflowing the solder material to electronically connect the contact pad of the magnetoresistance sensor die with a corresponding contact of a printed circuit substrate.

7. The method of claim 6, comprising reducing the thickness of the die.

8. The method of claim 6, wherein the die is formed in a wafer comprising a plurality of additional dies.

9. The method of claim 8, comprising cutting the die and the additional dies form the wafer prior to reflowing the solder material.

10. The method of claim 6, wherein the contact pad is suitable for wire bonding prior to application of the solderable layer.

11. The method of claim 6, wherein the solderable layer comprises electroless nickel.

12. The position and orientation sensor assembly of claim 1, wherein at least one solderable layer comprises electroless nickel, the corrosion resistance layer comprises gold, and the diffusion barrier layer comprises electroless nickel.

13. The position and orientation sensor assembly of claim 1, wherein the diffusion barrier layer comprises a thickness ranging from 500 Å to 1000 Å.

14. The position and orientation sensor assembly of claim 1, wherein the corrosion resistance layer comprises a thickness ranging from 500 Å to 1000 Å.

15. The position and orientation sensor assembly of claim 1, wherein the magnetoresistance sensor array comprises a first thickness of 200 micron or less, the adhesion promoter layer comprises a second thickness between 10 nm and 100 nm, the at least one solderable layer comprises a third thickness ranging from 3 micron to 5 micron, the diffusion barrier comprises a fourth thickness ranging from 500 Å to 1000 Å, and the corrosion resistance layer comprises a fifth thickness ranging from 500 Å to 1000 Å.

16. The position and orientation sensor assembly of claim 1, wherein the adhesion promoter layer comprises a thickness ranging from 10 nm to 100 nm.

17. The position and orientation sensor assembly of claim 1, wherein the at least one solderable layer comprises a thickness ranging from 3 micron to 5 micron.

18. The position and orientation sensor assembly of claim 1, wherein the magnetoresistance sensor array comprises a thickness of 200 micron or less.

19. The position and orientation sensor assembly of claim 1, wherein the position and orientation sensor assembly comprises a width of 0.4 mm.

* * * * *